United States Patent [19]

Adams

[11] 4,158,360
[45] Jun. 19, 1979

[54] EXPIRATORY FLOW METER

[75] Inventor: Jim M. Adams, Mt. Pleasant, S.C.

[73] Assignee: Projects in Health, Inc., Princeton, N.J.

[21] Appl. No.: 872,698

[22] Filed: Jan. 26, 1978

[51] Int. Cl.² ............................................. A61B 5/08
[52] U.S. Cl. ..................................... 128/725; 73/209; 73/211; 272/99
[58] Field of Search ................ 128/2.08, 2.07; 272/99; 73/209, 211, 239

[56] References Cited

U.S. PATENT DOCUMENTS

| 3,411,357 | 11/1968 | Childs | 73/209 |
| 3,633,421 | 1/1972 | Phillips | 73/209 |
| 3,695,608 | 10/1972 | Hanson | 272/99 |
| 3,822,699 | 7/1974 | Cleary | 128/2.08 |
| 3,871,364 | 3/1975 | Boehringer | 128/2.08 |
| 3,908,987 | 9/1975 | Boehringer | 272/99 |
| 4,025,070 | 5/1977 | McGull et al. | 272/99 |

Primary Examiner—Lee S. Cohen
Attorney, Agent, or Firm—Wolder, Gross & Yavner

[57] ABSTRACT

A peak expiratory flow meter device for indicating airway obstruction in a patient. The device includes an elongated channel arranged perpendicularly to a mouthpiece, at the end of which an adjustable orifice is disposed. A float moves within the channel in response to expiration from the patient. A removable pin is provided with the channel for accommodating various ranges of expiration, and for the same general reason, rotatable discs are provided to partially cover the orifice.

9 Claims, 5 Drawing Figures

EXPIRATORY FLOW METER

This invention relates generally to expiration flow rate measuring devices and more particularly to such devices which may be self-administered and which are adjustable in their range of measurement.

Peak expiratory flow rate is a good general indicator of the presence or absence of airway obstruction. Such a rate measurement is also determinative of responsiveness to bronchodilators and it is known that airway obstruction associated with lung disease is measurable long before symptoms may appear.

The measurement of peak expiratory flow rate could therefore be an effective medical tool if it could offer a quick, effective screening technique for presumably normal subjects away from the hospital and physician's office. Furthermore, such a device would be particularly useful in factories and as part of health survey programs on a regular basis.

Furthermore, in connection with lung disease, it is particularly important to determine the effectiveness of a prescribed drug without the necessity for hospitalization or constant visits to a physician's office. Expiratory flow rate is also indicative of the severity of an asthmatic attack.

Attempts at measuring devices such as the present invention have been made, but suffer from the disadvantages of cumbersome construction, lack of a compact design, complexity of operation effectively prohibiting home use and lack of sufficient accuracy.

Accordingly, a primary object of the present invention is to provide a compact, lightweight construction, peak expiratory flow meter which is simple to operate and yet efficient and accurate in its measurement.

A further object of the present invention is to provide a peak expiratory flow meter which may be adjusted in its range of measurement and accommodated for varying patient ages and conditions.

These and other objects of the present invention are accomplished in a peak expiratory flow meter according to the present invention which features a mouthpiece, an elongated channel substantially perpendicular to the mouthpiece and an orifice member disposed substantially in-line with the mouthpiece. The orifice member defines a first orifice at its end furthest from the mouthpiece, and the orifice is adjustable by means of a pair of discs, separately rotatable to either occlude the first orifice or lessen its effective opening. A float moves within the elongated channel in response to expiration from the patient and a removable pin prevents downward motion of the float within the channel, depending upon the range of expiration expected from the patient. The float in a preferred embodiment is a metal ball moving within a central race defined by the channel, and the channel is constantly wider as it elongates further from the mouthpiece in order to make it more difficult to move the float. The mouthpiece includes means for accommodating a disposable mouthpiece cover, thereby enabling use by more than one person, since the patient inspires air from outside the device before exhaling therethrough.

Other objects, features and advantages of the present invention will be apparent by reference to the following more detailed description of a preferred, but nonetheless illustrative, embodiment of the present invention with reference also to the accompanying drawings, wherein.

Figure 1:
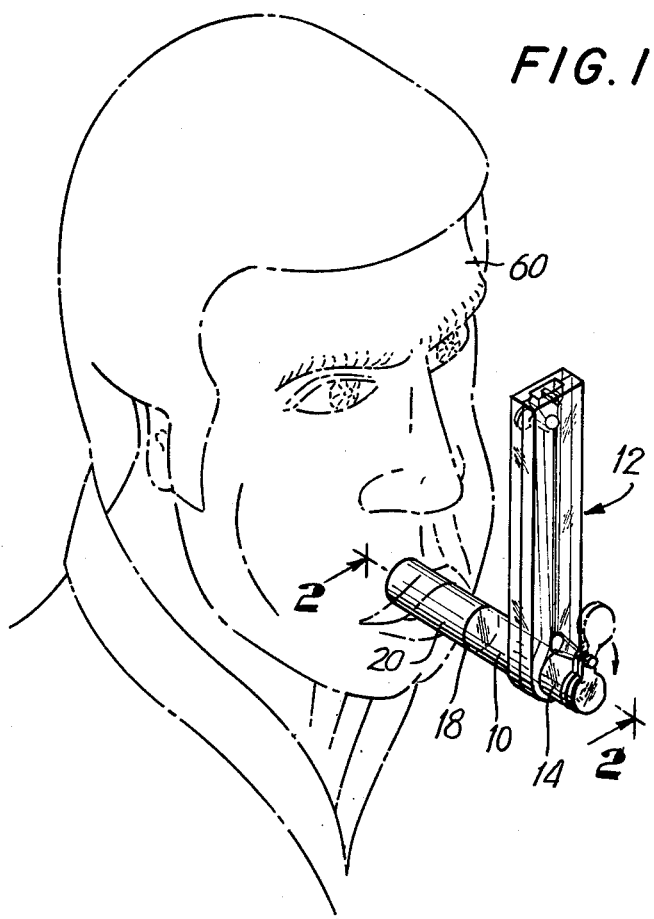
FIG. 1 is an isometric representation of a peak expiratory flow meter according to the present invention showing particularly the device in use and adjustment capability of the orifice thereof.

Referring to the drawings, a peak expiratory flow meter is shown to include a mouthpiece 10, and an elongated channel, generally designated 12, disposed substantially perpendicularly to the mouthpiece, and an orifice member 14 disposed substantially in-line with mouthpiece 10. The mouthpiece 10 is constructed to define a mouthpiece opening 16 and a stepped outer surface 18. The stepped outer surface is structured to accommodate a disposable mouthpiece cover 20., so that different patients are able to use the same device. The mouthpiece cover 20 may be paper or plastic or any suitable material and the expiratory meter itself is preferably of plastic or glass.

Figure 2:
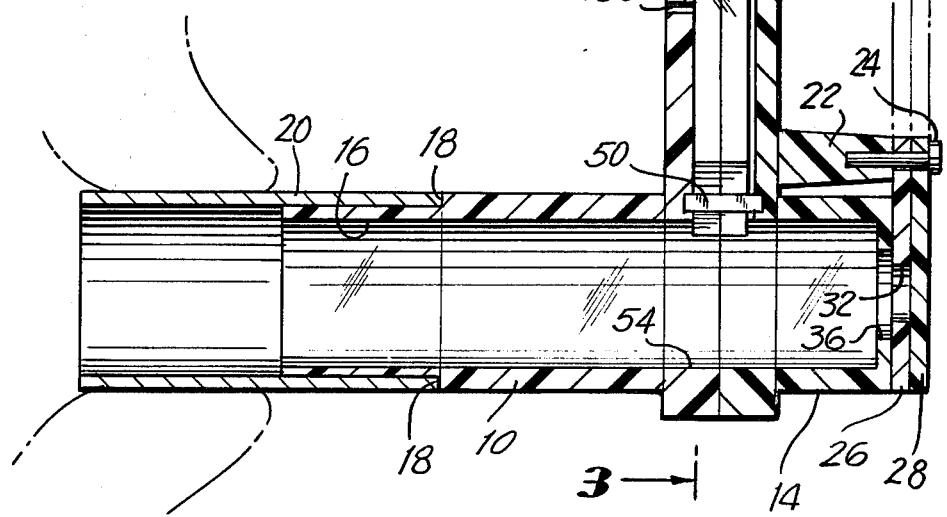
FIG. 2 is a side, sectional view of the present invention, taken along the line 2—2 of FIG. 1 and showing particularly the construction thereof and the use of range adjusting pin for the channel thereof.

The orifice member 14 (FIG. 2) includes an upper member 22 into which is inserted a disc pin 24 for holding a pair of rotatable discs 26, 28 at the end of the orifice member. Disc 28 is an occluding disc which may be rotated by means of pin 24 to a position shown by ghost lines 30. In this position, the orifice of the device is determined by orifice 32 defined by second orifice disc 26. Likewise, with both occluding disc 28 and second orifice disc 26 rotated by means of pin 24 to a position shown by ghost lines 34, 32, the orifice of the device will be determined by first orifice 36, as shown in FIG. 2.

The channel 12 includes an elongated base structure 38 defining a channel opening 40 which is constantly wider (FIG. 3) as the channel elongates further from mouthpiece 10. Still further, channel opening 40 includes a constant diameter race 42 extending the length of the channel to accommodate and control motion of a float 44 (FIG. 3), whose motion is controlled by operation of the device. The float 44 may be in the form of a metal ball or any other material useable in the preferred construction. Channel 12 still further defines a plurality of channel openings 46a, 46b, 46c, 46d, 46e, as shown in FIG. 2. Such channel openings are designed to engage removable pin 48, which, as shown in FIG. 2 is provided to prevent downward motion of float 44, depending upon the range of the device selected by the user. Channel 12 also includes a bottom stop 50 and a top stop 52, which respectively prohibit entrance of float 44 to primary orifice 54 defined at the intersection of mouthpiece 10 and channel 12, and to prevent removal of float 44 from the end of channel 12 furthest from the mouthpiece.

Figure 4:
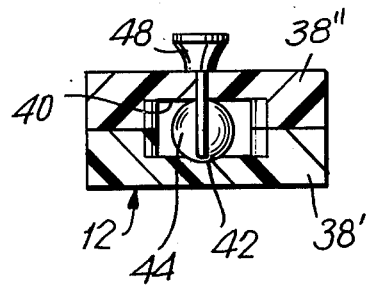
FIG. 4 is a sectional view of the channel, taken along the line 4—4 of FIG. 3.

Channel 12 has its base structure 38 shown in two mating halves 38' and 38" (FIG. 4), but it may be formed in a unitary mold or by any other convenient manufacturing process.

In order to more fully describe the present invention, a description of its operation and use will now be provided.

Defining the position of orifice discs 26, 28, as shown in FIG. 2 as "total occulsion", rotation of disc 28 to its ghost line position of FIG. 2 as "partial occlusion" and rotation of both orifice discs 26, 28 to their ghost line positions of FIG. 2 as "open", the following table represents a typical flow chart for guiding use of the device:

Table 1
Peak Flow Index Gradation
(Peak expiratory flow-liters/min)

| | |
|---|---|
| Low range (65-175) | |
| Orifice caliber: total occlusion | |
| Position of metal ball: | PEF |
| Position #1 | 65 |
| Position #2 | 125 |
| Position #3 | 175 |
| Medium range (175-325) | |
| Orifice caliber: partial occlusion | |
| Position of metal ball: | |
| Position #1 | 175 |
| Position #2 | 250 |
| Position #3 | 325 |
| High range (325-525) | |
| Orifice caliber: open | |
| Position of metal ball: | |
| Position #1 | 325 |
| Position #2 | 425 |
| Position #3 | 525 and above |

Also, the following charts represent spirometry in males, females and children to guide initial position of the orifice discs and pin 48:

Table 2
Spirometry in Normal Males
(Peak expiratory flow-liters/min)
(approximate values)

| | Height (inches) | | | | |
|---|---|---|---|---|---|
| Age | 60" | 65" | 70" | 75" | 80" |
| 20 | 554 | 602 | 649 | 693 | 740 |
| 30 | 532 | 577 | 622 | 664 | 710 |
| 40 | 509 | 552 | 596 | 636 | 680 |
| 50 | 486 | 527 | 569 | 607 | 649 |
| 60 | 463 | 502 | 542 | 578 | 618 |
| 70 | 440 | 477 | 515 | 550 | 587 |

Table 3
Spirometry in Normal Females
(Peak expiratory flow-liters/min)
(approximate values)

| | Height (inches) | | | | |
|---|---|---|---|---|---|
| Age | 55" | 60" | 65" | 70" | 75" |
| 20 | 390 | 423 | 460 | 496 | 529 |
| 30 | 380 | 413 | 448 | 483 | 516 |
| 40 | 370 | 402 | 436 | 470 | 502 |
| 50 | 360 | 391 | 424 | 457 | 488 |
| 60 | 350 | 380 | 412 | 445 | 475 |
| 70 | 340 | 369 | 400 | 432 | 461 |

Table 4
Spirometry in Normal Children and Adolescents
(Peak expiratory flow-liters/min)
(approximate values)

| Height (inches) | Males | Females |
|---|---|---|
| 43" | 147 | 147 |
| 44" | 160 | 160 |
| 45" | 173 | 173 |
| 46" | 187 | 187 |
| 47" | 200 | 200 |
| 48" | 214 | 214 |
| 49" | 227 | 227 |
| 50" | 240 | 240 |
| 51" | 254 | 254 |
| 52" | 267 | 267 |
| 53" | 280 | 280 |
| 54" | 293 | 293 |
| 55" | 307 | 307 |
| 56" | 320 | 320 |
| 57" | 334 | 334 |
| 58" | 347 | 347 |
| 59" | 360 | 360 |
| 60" | 373 | 373 |
| 61" | 387 | 387 |
| 62" | 400 | 400 |
| 63" | 413 | 413 |
| 64" | 427 | 427 |
| 65" | 440 | 440 |
| 66" | 454 | 454 |
| 67" | 467 | 467 |

Figure 3:
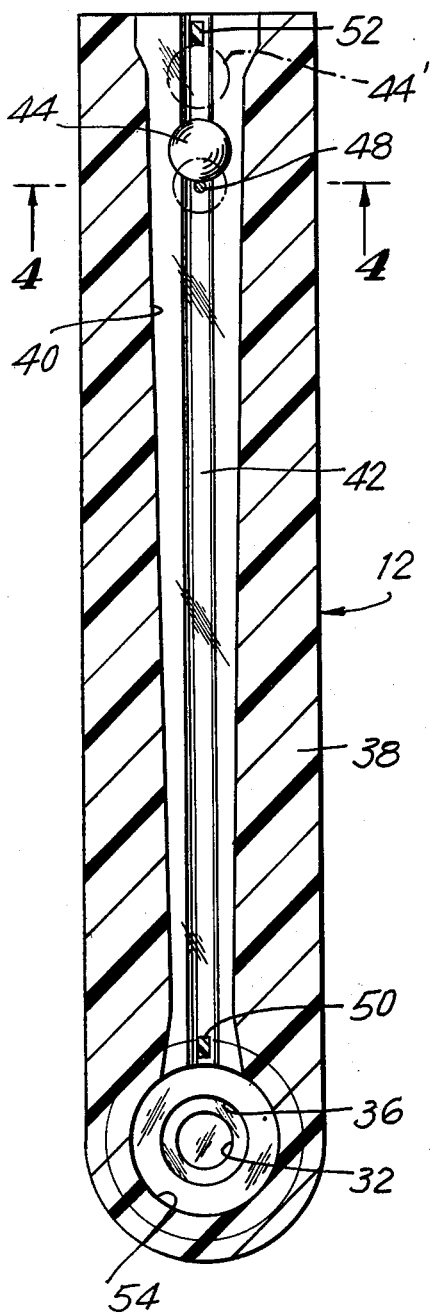
FIG. 3 is a front sectional view of the present invention taken along the line 3—3 of FIG. 2 and showing particularly the channel construction thereof.

Using the above predicted values, peak flow index in normal subjects according to their sex, age and height, may be determined. Before the patient 60 exhales into the device, the orifice caliber may be positioned, and the float positioned by means of pin 48. For example, if the patient is a 40 year old male, 5'10" in height, the predicted normal peak airflow will be 596 liters per minute. Accordingly, Table 1 is consulted to show the degree of occulsion and position of the flow such that both discs 26 and 28 will be rotated to nonoperating position or an orifice caliber designated "open". The float 44 will be located at "position #3", or the highest of the three ranges, shown in FIG. 3, wherein the extent of travel of float 44 is between the solid float position shown and the position 44' shown in ghost lines. This range is determined by position of pin 48, as shown in FIG. 3. Accordingly, stop 52 will prevent removal of float 44 from the device.

Figure 5:
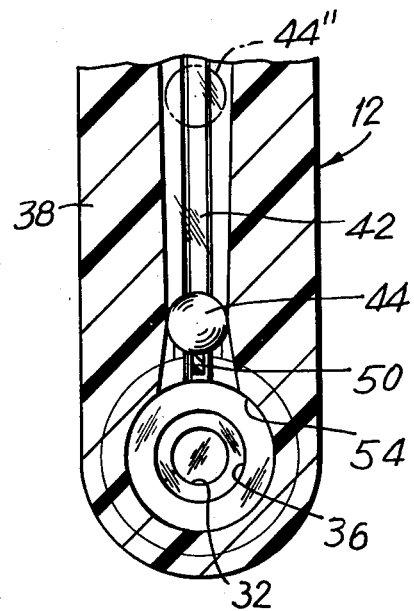
FIG. 5 is a partial view similar to that of FIG. 3, but showing the use of a defined range within the channel of the device.

Referring to FIG. 5, if the patient's condition and other factors had indicated "position #1", the range of travel would be between the position indicated by float 44 as shown and float 44" depicted by the ghost lines in FIG. 5. Stop 50 would prevent entrance of float 44 to primary orifice 54.

To obtain "position #1", the positioning pin 48 is simply removed from the device. To obtain "position #2", pin 48 is temporarily removed, and the device inverted so that the float 44 rolls to the top of the channel. The positioning pin 48 is then reinserted to maintain float 44 above a median position of the device. To obtain "position #3", pin 48 is temporarily removed and float 44 moved to the top of the channel by inverting the device. Pin 48 is then placed in the position shown at 48 in FIG. 3. Of course, a plurality of other positions are also obtainable by use of the various openings 46a-e shown in FIG. 2.

Also, in use of the device, the patient should receive clear instructions and be encouraged to make a maximum expiratory effort so that he exhales a single, short, powerful blast. Practice by the patient would both relax him and indicate whether or not readjustment of the device is necessary. For instance, if the patient fails in a practice attempt to move the ball at all, a lowering of pin 48 or a rotation into operating position of one or both of discs 26, 28, or another combination of adjustments would be indicated.

Accordingly, a simple, efficient and structurally sound device and accurate indication of peak expiratory flow is obtained by use of the present invention to determine the necessity for more definitive testing by other means. The device may be used without a hospital or physician's office environment and its simple design and operation provides a lasting quality for intended use.

What is claimed is:

1. A peak expiratory flow metering device for measuring airway obstruction in a patient indicating the necessity of more definitive testing comprising a mouthpiece, an elongated channel substantially perpendicular to said mouthpiece, an orifice member disposed substantially inline with said mouthpiece and defining a first orifice therein, a float located within said channel and for motion within said channel, said channel and orifice member in flow communication with said mouthpiece whereby said motion occurs in response to expiration from said patient, a plurality of channel openings defined by said channel at various points along said channel, means for preventing downward motion of said float within said channel including a removable pin positionable within said channel openings and means for selectively lessening said first orifice.

2. The invention according to claim 1 wherein said means for selectively lessening comprises a removable occluding disc for said first orifice.

3. The invention according to claim 2 wherein said means for selectively lessening further comprises a removable disc defining a second orifice smaller than said first orifice for lessening the effective orifice of said member.

4. The invention according to claim 1 wherein said float is a metal ball.

5. The invention according to claim 4 wherein said channel defines a constant diameter race in which said ball moves.

6. The invention according to claim 1 wherein said channel defines a channel opening which is constantly wider as the channel elongates further from said mouthpiece.

7. The invention according to claim 1 wherein said mouthpiece includes means for attaching a disposable mouthpiece cover.

8. The invention according to claim 1 wherein said mouthpiece and channel intersect in a primary orifice which includes means for preventing entrance of said float therein.

9. The invention according to claim 8 wherein said channel includes means for preventing removal of said float from the end of said channel furthest from said mouthpiece.

* * * * *